(12) United States Patent
Goohs et al.

(10) Patent No.: US 8,726,720 B2
(45) Date of Patent: May 20, 2014

(54) PARTICULATE MATTER MONITOR

(75) Inventors: Kevin J. Goohs, Greenfield, NH (US); Jeffrey Socha, Boylston, MA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 259 days.

(21) Appl. No.: 13/103,796

(22) Filed: May 9, 2011

(65) Prior Publication Data

US 2011/0271739 A1    Nov. 10, 2011

Related U.S. Application Data

(60) Provisional application No. 61/333,000, filed on May 10, 2010.

(51) Int. Cl.
*G01N 15/06* (2006.01)

(52) U.S. Cl.
USPC ....... 73/28.04; 73/28.01; 73/31.01; 73/31.05; 73/31.07

(58) Field of Classification Search
USPC ................... 73/28.01, 28.04; 209/138–143
See application file for complete search history.

(56) References Cited

U.S. PATENT DOCUMENTS

| | | | | |
|---|---|---|---|---|
| 2,051,567 A | * | 8/1936 | McGee | 55/419 |
| 2,091,514 A | * | 8/1937 | Meston | 209/139.1 |
| 2,461,584 A | * | 2/1949 | Andersen et al. | 209/139.1 |
| 2,494,465 A | * | 1/1950 | Watson et al. | 209/139.1 |
| 2,708,516 A | * | 5/1955 | Matheson et al. | 209/139.1 |
| 2,742,343 A | * | 4/1956 | McClure | 208/152 |
| 3,651,941 A | * | 3/1972 | Imris | 209/139.2 |
| 3,709,359 A | * | 1/1973 | Johnson | 209/138 |
| 4,132,634 A | * | 1/1979 | Rumpf et al. | 209/136 |
| 4,188,535 A | | 2/1980 | Wilson et al. | |
| 4,299,693 A | * | 11/1981 | Paulson | 209/3 |
| 4,587,024 A | | 5/1986 | Hayatdavoudi | |
| 4,657,667 A | * | 4/1987 | Etkin | 209/135 |
| 5,016,823 A | * | 5/1991 | Kato et al. | 241/5 |
| 6,739,456 B2 | * | 5/2004 | Svoronos et al. | 209/725 |
| 6,905,029 B2 | * | 6/2005 | Flagan | 209/210 |
| 2003/0160174 A1 | | 8/2003 | Grant | |
| 2004/0259267 A1 | | 12/2004 | Gundel | |
| 2008/0152547 A1 | * | 6/2008 | Hopke et al. | 422/109 |
| 2009/0065403 A1 | * | 3/2009 | Ito | 209/139.2 |
| 2010/0294863 A1 | * | 11/2010 | Schindler et al. | 241/24.1 |
| 2012/0111771 A1 | * | 5/2012 | Wang | 209/142 |

OTHER PUBLICATIONS

International Search Report, PCT/US2011/35773, dated Aug. 26, 2011, pp. 1.

* cited by examiner

*Primary Examiner* — John Fitzgerald
*Assistant Examiner* — Alexander Mercado
(74) *Attorney, Agent, or Firm* — Chapin IP Law, LLC

(57) ABSTRACT

A particulate monitoring system includes a conduit in which to a pass a fluid sample from an input port to an output port. The particulate monitoring system receives a fluid sample inputted to the conduit through the input port. The fluid sample can include different sizes of particulate matter. The particulate monitoring system controls a flow of the fluid sample through the conduit to age the particulate matter. Gravitational forces cause a portion of the particulate matter in the fluid sample to fall into a basin as opposed to being exhausted through the output port, which is disposed at a vertically higher level of the conduit than the input port. Thus, the particulate monitoring system outputs a portion of the original particulate matter in the fluid sample (e.g., particulate matter that does not drop into the basin out due to gravity) for analysis.

25 Claims, 7 Drawing Sheets

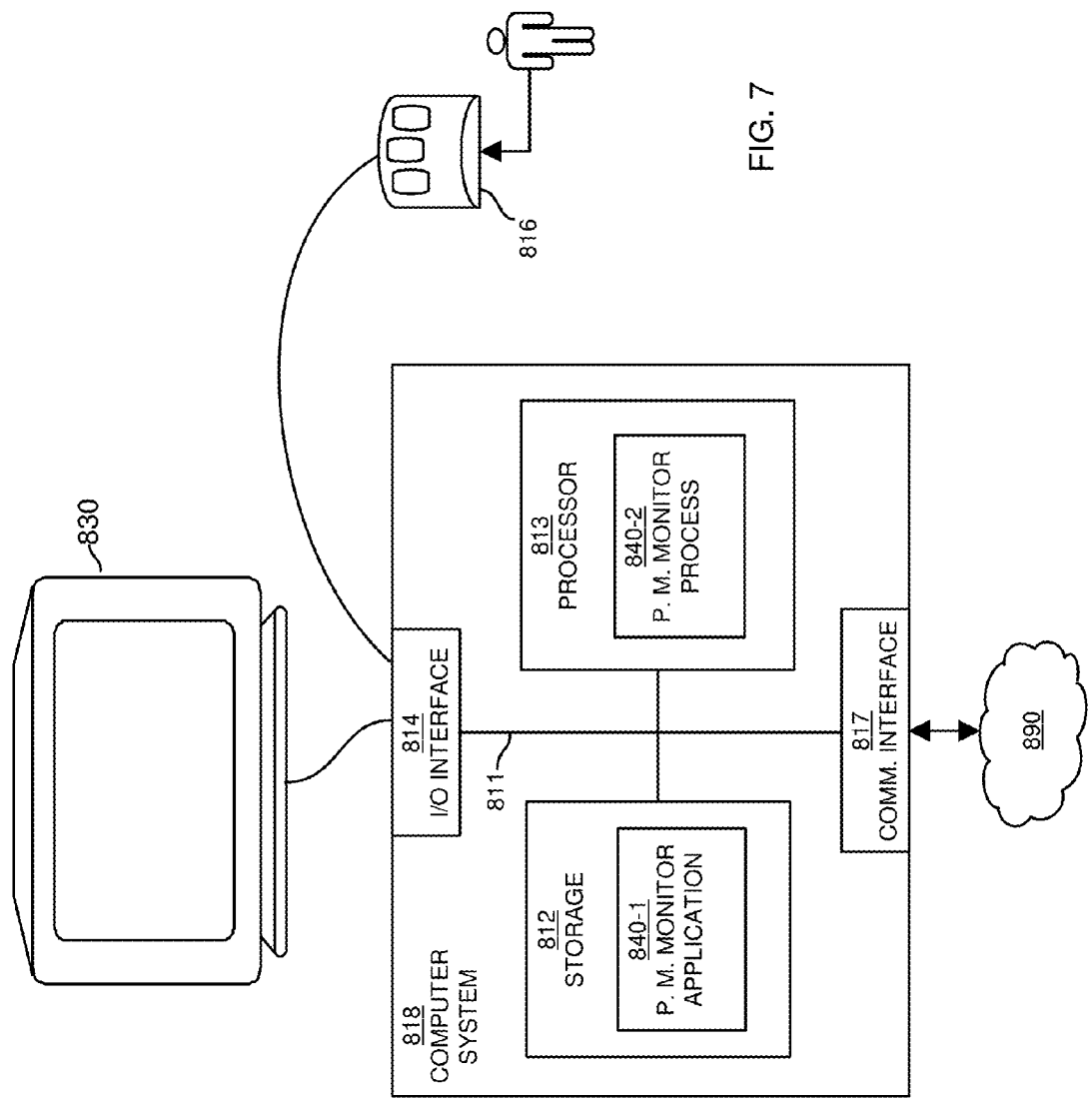

PARTICULATE MATTER MONITOR

RELATED APPLICATIONS

This application is related to and claims the benefit of earlier filed U.S. Provisional Patent Application Ser. No. 61/333,000 entitled "PARTICULATE MATTER EMISSIONS MONITORING SYSTEM," filed on May 10, 2010, the entire teachings of which are incorporated herein by this reference.

BACKGROUND

Continuous monitoring of the mass concentration of particulate matter from source emissions is becoming a growing requirement within the framework of clean air regulations in both the US and abroad. Of great interest is the desire to measure a particulate mass concentration in a form that simulates the source emission after it has equilibrated to ambient air conditions. This form of particulate matter is known as Total Primary Particulate (TPP) and is comprised of particulate matter that can be removed directly from a source through the use of filterable extraction plus particulate that can be created by condensation at a reference temperature from the remaining fluid stream.

The extraction, transport, conditioning and measurement of a sample from a source are critical processes necessary to provide consistent results and low downtime for service. Each of these processes gives rise to specific challenges, and with proper design, can be overcome and reduce instrumentation service intervals.

Through the past few decades the Unites States Environmental Protection Agency (EPA) has promulgated at least 15 reference methods for measuring particulate matter from source emissions. The root cause of this plethora of methodology stems from the varying conditions in which the EPA justified modifying the originating method (e.g., Method 5). As a result of these varied methods, instrumentation manufacturers have taken advantage of their ability to install and calibrate (correlate) a surrogate particulate matter measurement (e.g., light scattering, opacity, probe electrification) to one of the multitude of reference methods, which can vary in accuracy by an order of magnitude.

The concept of measuring TPP is not new to the art. A synonym for this methodology is known as dilution tunnel sampling whereby a sample is extracted from a source and diluted with filtered ambient air so that conventional ambient air samplers or analyzers can be used to measure the diluted concentration. By simultaneous measurement of the magnitude of dilution (dilution ratio), the measured concentration would be multiplied by the dilution ratio to calculate the actual concentration within the source. In the last 20 years prior art has documented this approach:
  i) SAMPLING, ANALYSIS, AND PROPERTIES OF PRIMARY PM-2.5: APPLICATION TO COAL-FIRED UTILITY BOILERS. DOE AWARD #: DE-FG2699-FT40583, FEBRUARY 2003; DILUTION TEST METHOD FOR DETERMINING PM2.5 AND PM10 MASS IN STACK GASES. ASTM WK8124~2008;
  ii) SOURCE CONTRIBUTIONS TO ATMOSPHERIC CARBON PARTICLE CONCENTRATIONS. G. R. CASS, CALIFORNIA INSTITUTE OF TECHNOLOGY, 1992; and
  iii) CONDITIONAL TEST METHOD 039, MEASUREMENT OF PM2.5 AND PM10 EMISSIONS BY DILUTION SAMPLING, USEPA, JULY 2004.

Particulate monitoring can be a complex process. Although reference methods are capable of operating within complex source emission environments, the operating period can be somewhat short-lived. Frequent cleaning of equipment and recovery of sample may be necessary.

These types of steps for a continuous monitor are unacceptable and therefore innovative approaches are required to extract, handle and condition a sample for the purpose of measurement. For example, the USEPA often requires the use of in-stack cyclones, which will separate, through inertia, the particles of interest for measurement and collect and remove larger particles that are not of interest. Such cyclones can only collect and remove unwanted particulate for a finite period of time. However, use of this approach is unacceptable from a service perspective for a continuous monitoring system whether it is for an in-stack cyclone or a post-diluted sample cyclone.

Another complexity for of particulate matter monitoring systems is that of the source environment. Although highly corrosive environments are expected, the larger challenge is to design a system such that it may be utilized in a water-saturated environment as well as very hot, dry environments. In a saturated environment, both particulate matter and water droplets less than approximately 40 micrometers need to be collected based on the theory that a droplet will have a 4:1 reduction in size and, when dried, will become a 10 micrometer particle—which may be of interest.

BRIEF DESCRIPTION

Embodiments herein deviate with respect to conventional particulate mass monitors and aging systems. For example, one embodiment herein includes a particulate monitoring system that relies at least in part on gravitational forces to separate different sizes of particulate matter in a vertically disposed conduit.

More specifically, in accordance with one embodiment, a particulate monitoring system receives a fluid sample inputted to a conduit through an input port. The fluid sample can include different sizes of particulate matter. During operation, the particulate monitoring system controls a flow of the fluid sample (such as a mixture of a flue gas sample and a dilution gas or other sample of interest) through the conduit to age the particulate matter in the fluid sample. Gravitational forces cause a portion of the particulate matter in the fluid sample to fall into a basin as opposed to being exhausted through an output port of the condition. The particulate monitoring system outputs a portion of the particulate matter (e.g., particulate matter that does not drop out due to gravity) from an output port of the conduit. The output port is disposed at a vertically higher level of the conduit than the input port. The particulate monitoring system monitors a presence of particulate matter outputted from the output port of the conduit.

As mentioned, one embodiment of the particulate monitoring system relies at least in part on gravitational forces to separate, in the conduit, heavier particles from lighter particles in the fluid sample. For example, the particulate matter ages as it passes though the conduit. Aging causes certain types of particulate matter in the fluid sample to become heavier and fall into the basin due to the gravitational forces. Aging causes certain particulate matter to become lighter and therefore pass through the output port for monitoring.

In accordance with another embodiment, the directional flow of the fluid sample passing from the input port to the output port of the conduit is substantially opposite to gravitational forces. In other words, the flow of gas or liquid in the fluid sample applies a force on the particulate matter in the fluid sample to pass from the input port to the output port. However, gravitational forces pull the particulate matter in the fluid sample in a substantially opposite direction of the gas or liquid flow of the fluid sample. If the gravitational forces are greater than the force on the particulate matter due to flow of the fluid in the fluid sample, the particulate matter does not exit the output port of the conduit. If the forces applied to the particulate matter by the flow of the fluid in the fluid sample are greater than the gravitational forces, the particulate matter exits the output port of the conduit.

The particulate monitoring system can be configured to include a flow controller to control a flow rate of the fluid sample from the input port to the output port through the conduit to separate the heavier particles and the lighter particles from each other. This process can include outputting the lighter particles from the output port and settling the heavier particles in a basin disposed at a vertically lower level than a level of the input port of the conduit.

In one embodiment, the particulate monitoring system and any of one or more controllers therein controls a rate of the fluid sample through the conduit such that the residence time of at least a portion of the particulate matter in the conduit is above a threshold value.

The particulate monitoring system also can control a rate of the fluid sample through the conduit to control which portion of the different sizes of particulate matter in the fluid sample overcome the gravitational forces and pass through the output port of the conduit.

In addition to a flow of the fluid sample, the particulate monitoring system can be configured to control other environmental parameters. For example, the particulate monitoring system can be configured to control a temperature of the fluid sample in the conduit; the particulate monitoring system can be configured to control a relative humidity of the fluid sample in the conduit; etc.

Via control of environmental parameters of the fluid sample in the conduit, the particulate monitoring system is able to simulate aging of the particulate matter that would occur when the fluid sample is otherwise exhausted into the atmosphere. As discussed above, via controlling the environmental parameters in the particulate monitor system, a portion of particles in the fluid sample received from the input port physically becomes heavier and falls into a basin due to gravitational forces as opposed to being otherwise outputted from the output port with lighter particles that are not heavy enough to settle in the basin due to the gravitational forces. In other words, aging the received particulate matter can change an aerodynamic equivalent diameter of the particle to a larger value during residence in the conduit, which cause the particle to fall into a basin as opposed to being exhausted out of the conduit. Conversely, aging of a received particulate matter can change an aerodynamic equivalent diameter of the particle to a smaller value during residence in the conduit, which cause the particle to be exhausted out of the conduit pass through output port as opposed to settling in a basin. Particulate matter as discussed herein can be a single particle or multiple particles.

In one embodiment, the output port or other portion of the conduit is tapered to focus the fluid sample for particulate matter monitoring. Tapering the conduit and/or output port increases a density of the fluid sample for analysis by a mass monitoring system.

Monitoring and analyzing the presence of particulate matter outputted from the output port of the conduit can include measuring a particle size distribution of the particulate matter outputted from the output port through the tapered conduit.

In accordance with yet another embodiment, the fluid sample passed through the conduit can be a mixture of a dilution gas and a received flue sample. The particulate monitoring system can monitor a sensor (e.g., a relative humidity sensor or dew point sensor to monitor water in the fluid sample) in the conduit. The particulate monitoring system controls or adjusts a dilution ratio of the dilution gas mixed with the received flue gas sample to maintain the relative humidity of the fluid sample in the conduit to be within a desired range or level.

A mass monitoring system monitors a presence of particulate matter in the diluted flue gas sample passing through and outputted from the conduit. In one embodiment, the particulate monitoring system sets a rate of inputting the fluid sample into the conduit to be substantially constant and adjusts the relative humidity of the dilution gas to keep the relative humidity of the fluid sample within a desired range.

These and other more specific embodiments are disclosed in more detail below.

It is to be understood that embodiments of the system, method, apparatus, etc., as discussed herein can be embodied strictly as hardware, as a hybrid of software and hardware, or as software alone such as within a processor, or within an operating system or a within a software application.

As discussed above, techniques herein are well suited for use in particulate monitoring systems. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where appropriate, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

FIG. 1 is an example diagram of a system for aging particulate matter in a fluid sample according to embodiments herein.

FIG. 2 is an example diagram of a system for aging particulate matter in a fluid sample according to embodiments herein.

FIG. 3 is a theoretical example graph illustrating settling velocity versus aerodynamic equivalent diameter of particulate matter according to embodiments herein.

FIG. 4 is an example diagram of a particulate monitor system including components to control a relative humidity or dew point of a fluid sample according to embodiments herein.

FIG. 7 is an example diagram illustrating a computer for executing software instructions to carry out operations according to embodiments herein.

DETAILED DESCRIPTION

An example particulate monitoring system includes a conduit in which to a pass a fluid sample. The particulate monitoring system receives a fluid sample inputted to the conduit through an input port. The fluid sample can include different sizes of particulate matter. The particulate monitoring system controls a flow of the fluid sample through the conduit to age the particulate matter. Characteristics of the particulate matter can change while resident within the conduit. In opposition to a flow of the fluid in the fluid sample towards the output port, gravitational forces cause a portion of the particulate matter in the fluid sample to fall into a basin as opposed to being exhausted through the output port. The output port is disposed at a vertically higher level of the conduit than the input port. The particulate monitoring system outputs, from the output port, a portion of the original particulate matter in the fluid sample (e.g., particulate matter that does not drop into the basin out due to gravity) for analysis.

Figure 1:
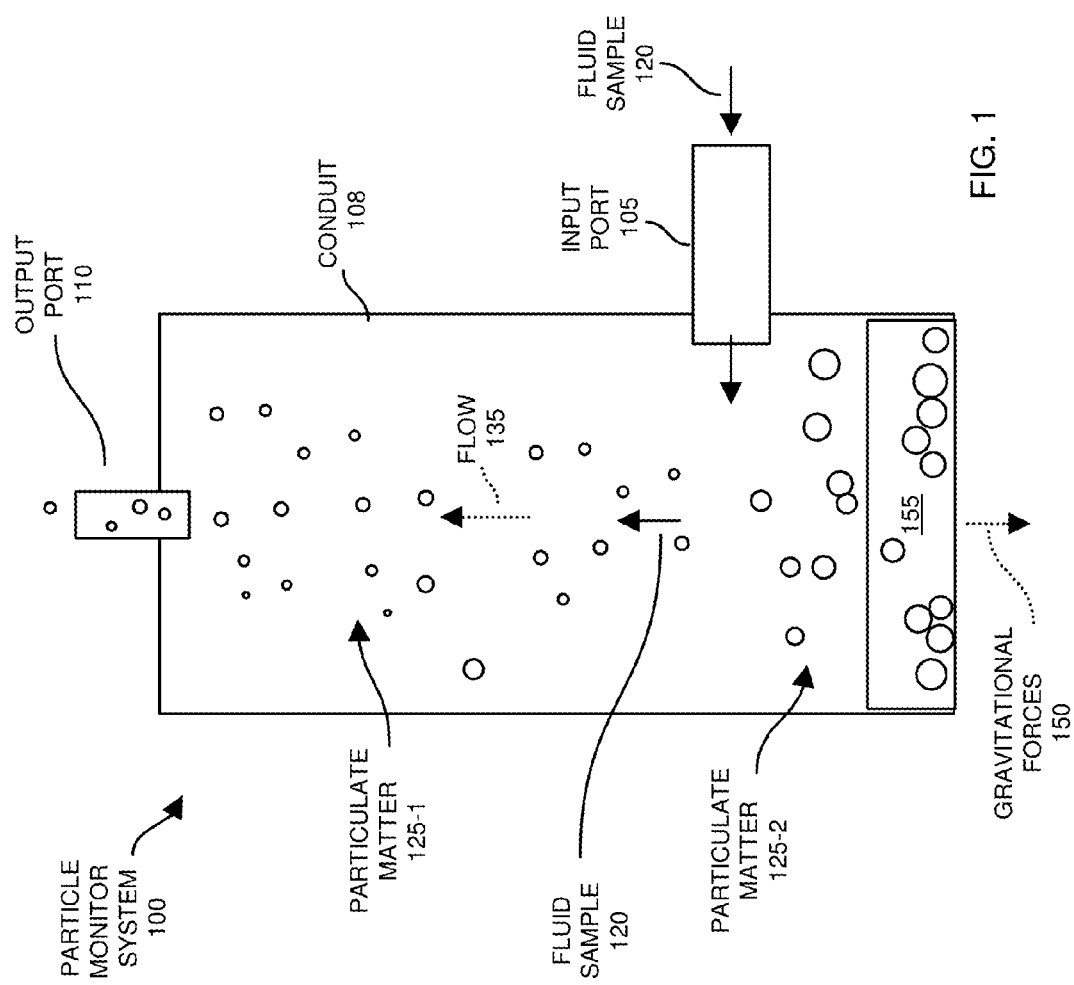

Now, more particularly, FIG. 1 is an example diagram illustrating a particulate monitor system 100 according to embodiments herein. As shown, particulate monitor system 100 includes an input port 105, a conduit 108, and an output port 110.

In this general embodiment, the particulate monitor system 100 receives fluid sample 120. The fluid sample 120 is inputted through input port 105 and passes through conduit 108 to output port 110. The conduit 108 acts as an aging vessel for the particulate matter 125 as it passes or resides in conduit 108.

Note that the fluid sample 120 can include a liquid and or gas as well as different sizes of particulate matter of any suitable type. For example, in one embodiment, the fluid sample 120 can be received as a mixture of: i) a flue gas sample (e.g., as received from a smoke stack) and ii) a dilution gas. The flue gas sample can include particulate matter for analyzing.

In one embodiment, the particulate monitor system 100 controls a rate of the flow of the received fluid sample 120 into the input port 105. In one embodiment, the flow rate of the fluid sample 120 is controlled within a desired range in order to ensure that the particulate matter 125 in the fluid sample 120 resides in the conduit 108 for at least a minimum threshold time.

In accordance with another embodiment, the flow rate of the fluid sample 120 is controlled in order to select which sizes of particulate matter in the fluid sample 120 passes through the conduit 108 through the output port 110.

For example, as indicated by directional flow 135, gases and/or liquid in the fluid sample 120 flow in a substantially vertical manner through conduit 108 to output port 110. The gas and/or liquid in the fluid sample 120 imparts an upward force on the particulate matter to push it through the conduit 108 and out of the output port 110 for analysis.

The output port 110 is disposed at a vertically higher level of the conduit 108 than the input port 105. As will be discussed in more detail below, output port 110 can include a mass monitoring system to determine a mass concentration associated with the particulate matter in fluid sample. In one embodiment, the system as discussed herein can include or be used in a manner to detect a size distribution of one or more particles in the particulate matter. For example, the monitoring system can measure different sizes of particulate matter above a threshold value passing through the conduit 108 and output port 110. Particulate matter as discussed herein can be a single particle or multiple particles.

As mentioned, the directional flow 135 of gas and/or liquid present in the fluid sample 120 imparts an upward force on the particulate matter 125 in the fluid sample 120. In a substantially opposite direction, gravitational forces 150 exert a downward force on the particulate matter 125 towards basin 155. If the gravitational forces 150 on particulate matter are greater than the force exerted due to flow of the fluid sample 120, the particulate matter does not exit the output port of the conduit but instead falls into basin 155. If the forces applied to the particulate matter due to the flow of the fluid sample 120 are greater than the gravitational forces 150, the particulate matter exits the output port 110 of the conduit 108.

In one embodiment, the particulate matter 125 passes though the conduit 108 and out of output port 110 or falls into the basin 155 depending on the effective aerodynamic equivalent size of the particulate matter. For example, a majority of the lighter particulate matter or particulate matter 125-1, which has an aerodynamic equivalent diameter below a threshold value, passes through conduit 108 and out of output port 110. A majority of the heavier particulate matter or particulate matter 125-2, which has an aerodynamic equivalent diameter above the threshold value, does not pass through conduit 108 and out of output port 110. Accordingly, the particulate monitor system 100 uses gravitational forces 150 and gas flow forces of the fluid sample 120 to separate heavier particulate matter 125-2 from lighter particulate matter 125-1.

The gravitational forces 150 applied to the particulate matter 125 are relatively constant. The particulate monitoring system 100 can control a rate (e.g., volume) of the fluid sample 120 passing through the conduit 108 to control which portion of the different sizes of particulate matter overcome the gravitational forces and pass through the output port of the conduit.

For example, higher flow rates of passing the fluid sample 120 through conduit 108 causes more of the particles in the fluid sample 120 to exit conduit 108 through the output port 110. Lower flow rates of passing the fluid sample 120 through conduit 108 causes more of the particles in the fluid sample 120 to fall into basin 155 as opposed to being outputted from output port 110.

Note again that the particulate matter 125 in the fluid sample 120 ages as it passes though the conduit. The process of aging causes certain types of particulate matter in the fluid sample to become heavier during its residence within conduit 108, causing it to fall into the basin 155 due to the gravitational forces 150.

Aging of particulate matter in the fluid sample 120 also can cause certain particulate matter 125 to become lighter during residence in conduit 108, causing it pass through the output port 110 for mass monitoring. Environmental parameters of the fluid sample 120 in the conduit 108 can be controlled to cause different types of aging to respective particulate matter 125 in the fluid sample 120.

Environmental parameters controlled by the particulate monitor system 100 can include the temperature of the fluid sample in the conduit; the relative humidity of the fluid sample 120; velocity of the fluid sample 120 through the conduit 108; etc. Via control of environmental parameters of the fluid sample 120 in the conduit 108, the particulate monitoring system 100 is able to simulate aging of the particulate matter 125 that otherwise occurs when exhausted into the atmosphere.

In one embodiment, the particulate monitor system 100 controls the pressure in the conduit 108 to be in a range such as 1.0+/−0.5 atmospheres, although the pressure of the fluid sample 120 in conduit 108 can be any suitable value.

In accordance with another embodiment, the particulate monitor system 100 controls the temperature in the conduit 108 to be approximately 30 degrees during TPP type simulations.

In accordance with other embodiments, the particulate monitor system 100 controls the temperature of the fluid sample in the conduit 108 to be any suitable temperature such as between 25 and 180 degrees Celsius.

Figure 2:
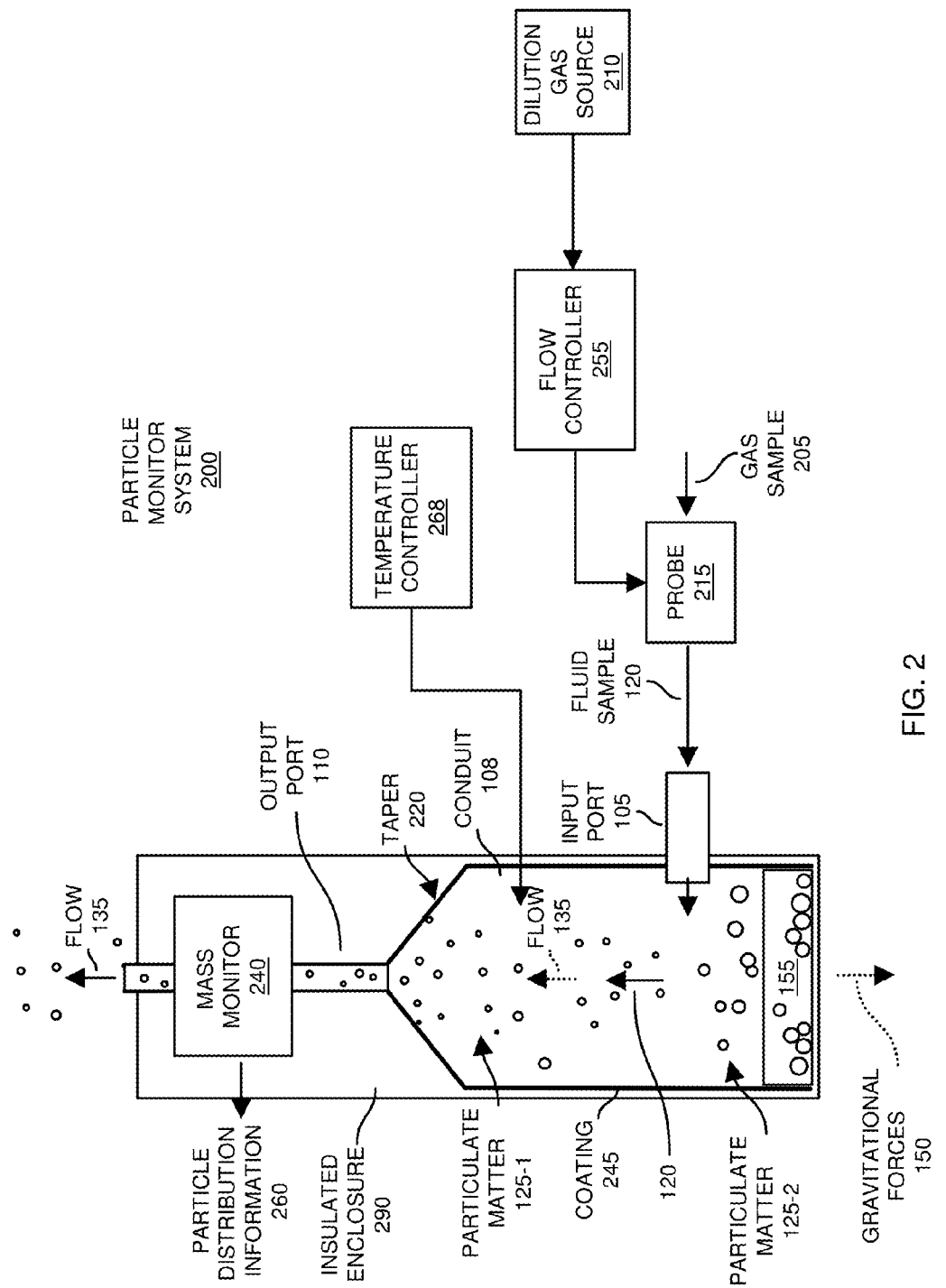

FIG. 2 is an example diagram of a system 200 for aging particulate matter in a received gas sample according to embodiments herein.

By way of a non-limiting example, note that components such as conduit 108, output port 110, mass monitor 240, etc., or portions thereof can reside within an insulated enclosure 290.

As shown, particulate monitor system 200 receives gas sample 205 from a source such as a flue via probe 215. Probe 205 can be heated. In one embodiment, the probe 205 resides within a respective flue (e.g., smokestack or other exhaust system outputting particulate matter of interest).

The particulate monitor system 200 can include dilution gas source 210 for providing particle-free dry air, nitrogen, etc., to dilute the gas sample 205.

Particulate monitor system 200 includes flow controller 255 (e.g., one or more control valves, conduits, etc.) to control a flow of the gas sample 205 and/or control dilution of the gas sample 205 with dilution gas received from dilution gas source 210. Fluid sample 120 is a mixture or combination of gas sample 205 mixed with dilution gas received from dilution gas source 210.

Particulate monitor system 200 can include temperature controller 268. Temperature controller 268 can be configured to monitor a temperature of the fluid sample 120 in conduit 108 and regulate the temperature of the fluid sample 120 in the conduit 108 within a desired range.

By way of a non-limiting example, the particulate monitor system 200 can include flow controller 255 to dilute the gas sample 205 based on a ratio of between 10:1 (e.g., ten parts dilution gas to one part gas sample 205) and 25:1 (e.g., twenty five parts dilution gas to one part gas sample 205). Thus, one part of the gas sample 205 can be diluted with between ten and twenty-five parts of dilution gas. In accordance with other embodiments, note that the gas sample 205 can be diluted using any suitable ratio for particulate mass monitoring as discussed herein.

In accordance with further embodiments, the dilution gas received from the dilution gas source 210 can have a dew point between −40 and −70 degree Celsius. However, note that the dew point of the dilution gas can be any appropriate value for a respective application of particulate monitor system 200.

As previously discussed, the fluid sample 120 passes through conduit 108. The particulate matter 125 ages while passing through conduit 108. A first portion of the particulate matter 125-1 in fluid sample 120 passes through output port 110 while a second portion of particulate matter 125-2 falls into basin 155.

Depending on the embodiment, conduit 108 can be made of any suitable material such as stainless steel, plastic, etc. The inner walls of conduit 108 (to which the fluid sample is exposed) can include a coating 245 of material such as glass, epoxy, etc. Certain types of coatings can prevent particulate matter from sticking as it passes through conduit 108.

In one embodiment, the output port 110 and/or respective portion of conduit 108 includes taper 220 to focus the fluid sample 120 for particulate monitoring via mass monitor 240.

The mass monitor 240 monitors the presence of particulate matter outputted from the output port 110 of the conduit 108. Mass monitor 240 can employ any suitable technique to monitor the fluid sample 120 for presence of particulate matter. For example, the mass monitor 240 can be configured to pass an optical signal though the passing fluid sample 120 and analyze scattered, reflected, absorption, etc., to determine respective distribution densities of one or more classes of different sized particles. Any suitable technique can be used to analyze the particulate matter.

Analysis of the passing fluid sample 120 by mass monitor 240 can include measuring a particle size distribution of the particulate matter in the fluid sample 120 and generating respective particle distribution information 260. The probability distribution information 260 can indicate the density of a group of particulate matter falling within a first size range; the probability distribution information 260 can indicate the density of a group of particulate matter falling within a second range; and so on.

In accordance with yet another embodiment, as mentioned, the fluid sample 120 in the conduit 108 can be a mixture of a dilution gas and a received flue gas sample 205 including particulate matter. The particulate monitoring system 200 can be configured to monitor a relative humidity of the fluid sample in the conduit 108. In accordance with such an embodiment, the particulate monitor system 200 controls a relative humidity of the dilution gas (as received from the dilution gas source 210) mixed with the received gas sample 205 to maintain the relative humidity of the fluid sample 120 in the conduit 108 to be within a desired range.

In one embodiment, the particulate monitor system 200 sets a rate of inputting the fluid sample 120 into the conduit 108 to be substantially constant.

One use of the particulate monitor systems as discussed herein is to simulate plume conditions after a flue gas has left a smoke stack and has been exposed to the atmosphere. Particle formation after leaving the stack can include a number of processes such as condensation growth, droplet evaporation, coagulation, agglomeration, enrichment, and saturation vapor pressure. These processes are part of the "aging" process of particulate matter. Controlling the environmental parameters and flow of the fluid sample in conduit 108 simulates the aging of particulate matter that would otherwise occur in the open atmosphere. Thus, it is possible to analyze aged particulate matter even though it has not been exhausted into the open air above a smokestack.

In one embodiment, in an effort to maintain consistency with which the aging occurs, a reference condition can be chosen—analogous to the laboratory reference conditions to which ambient PM2.5 samples are measured. A temperature and relative humidity of the fluid sample in the conduit 108 can be selected to be a constant value since variations in these parameters can affect aging.

As mentioned, via particulate monitor system 200, after particles have been extracted from an emission source (e.g., a flue) they encounter a region of dilution within the probe for the purpose of drying the particles to a reference condition further downstream. The fluid sample 120 (including respective particles) are delivered to the conduit 108. In one embodiment, the conduit 108 is vessel known as a vertical elutriator.

As mentioned, the conduit 108 gravitationally separates and removes particles of non-interest above a given aerodynamic equivalent size (or size range). The vertical conduit 108 enables remaining particles of interest (e.g., particulate matter that do not fall into basin 155 out due to gravity) to pass though output port 110 for mass measurement.

As mentioned, parameters such as temperature, relative humidity, and vertical fluid velocity conditions of the fluid sample 120 within the conduit 108 can be held near constant conditions (e.g., 30 deg C., 70% RH, and 0.00299 m/s) whilst the fluid sample 120 (e.g., a diluted gas sample) is aged in the conduit 108 for a desired residence time.

As discussed, embodiments herein permit a variable separation of particles by varying the vertical velocity of the fluid sample 120 towards a mass monitor 240. For example, the particulate monitor system 200 can set the flow rate to a first velocity setting in which a majority of particles above a first threshold value pass through output port 110 and are analyzed by mass monitor 240 to produce a first set of probability distribution information 260; the particulate monitor system 200 can set the flow rate to a second velocity setting in which a majority of particles above a second threshold value pass through output port 110 and are analyzed by mass monitor 240 to produce a second set of probability distribution information 260; and so on.

In one embodiment, the conduit 108 enables the particulate matter in gas sample 205 and the dilution gas to mix and/or react for a time period in excess of 10 seconds. In accordance with another embodiment, the flow rate of the fluid sample 120 can be controlled such that the residence time permits particulate matter aging in the fluid sample of approximately 1 or more minutes.

Figure 3:
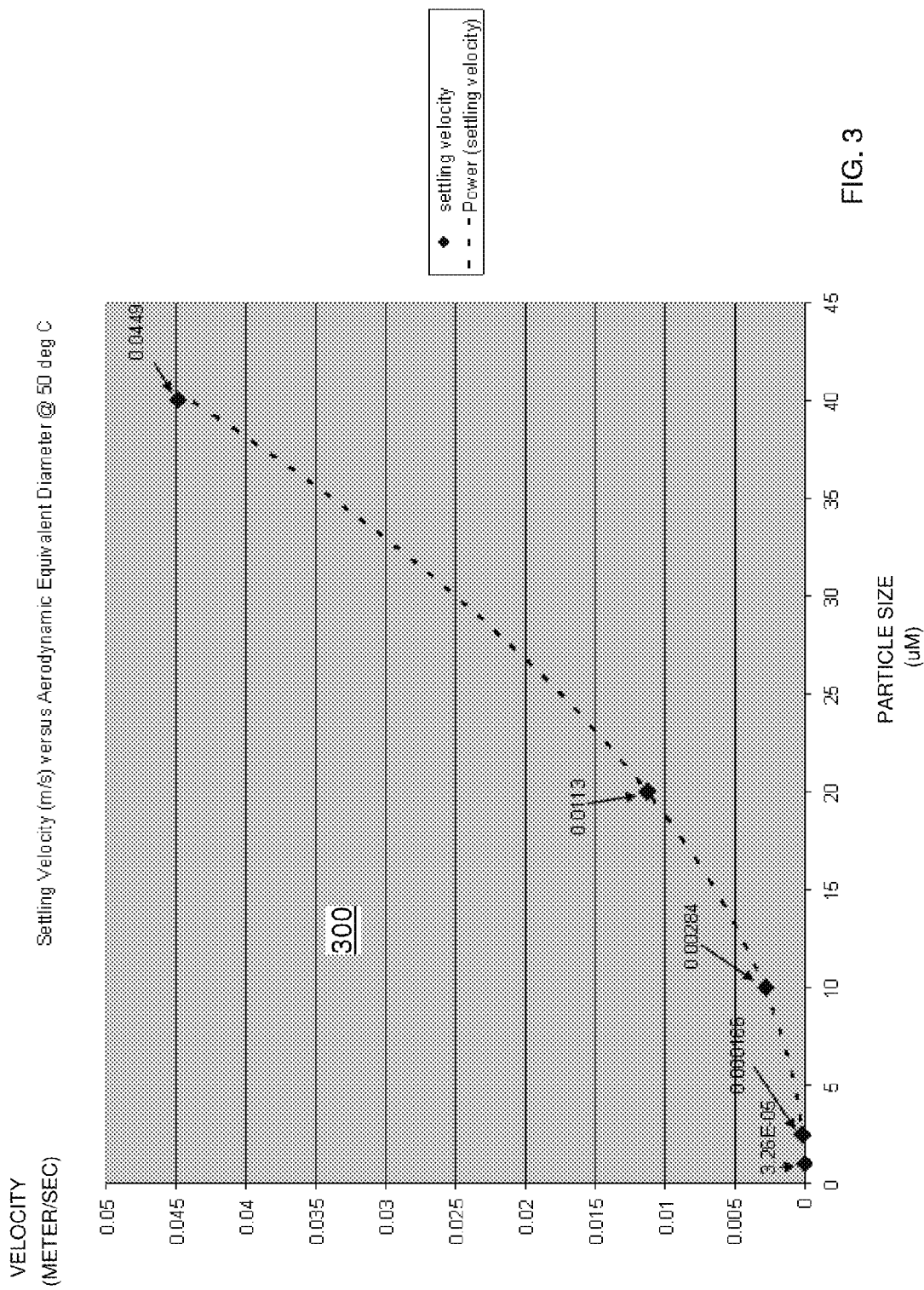

FIG. 3 is an example hypothetical graph illustrating aerodynamic equivalent diameter of particulate matter versus settling time at temperature 50 degrees Celsius and pressure of approximately one atmosphere according to embodiments herein. Conditions In general, graph 300 illustrates that particulate matter having a higher aerodynamic equivalent diameter has a higher settling velocity than do smaller aerodynamic equivalent diameter particles. Note that graph 300 takes into account power regression. To push the larger sized particulate matter in fluid sample 120 through the output port, an appropriate higher velocity of the gas and/or liquid in the fluid sample 120 is needed.

Graph 300 can be used to determine the rate at which to pass the fluid sample 120 through the conduit 120. For example, a user first determines a size of particles of interest to be analyzed in the fluid sample 120. The user then sets a rate of the fluid sample 120 to be above the corresponding settling velocity for the particulate matter of interest in order to push the particulate matter out through the output port 110. Note that different sized particles in the fluid sample 120 will have a different resident time in the conduit 108.

Example Embodiment

Note that each of the different parameters of this example embodiment are shown by way of non-limiting example only and that such parameters can be set to any suitable value depending on the embodiment.

In one non-limiting example embodiment of a particulate monitor system, the fluid sample 120 (e.g., diluted sample) is drawn or pushed into the input port 105 of the conduit 108 at a flow rate of approximately 1.88 liter per minute (0.000031 cubic meters per second).

The conduit 108 (e.g., particulate matter separation chamber) of the particulate monitor system can be configured to have an inside diameter of approximately 0.118 meters and a height of at least 0.03 meters for a minimum residence time of 10 seconds.

The cross sectional area of the conduit 108 (viewed from a direction of the flow 135), can be calculated from the inside diameter. For example, in this example embodiment, the cross-sectional are is 0.011 square meters. The sample flow rate is divided by the cross sectional area to calculate and upward velocity of the fluid sample 120. In this example, the upward velocity of the fluid sample 120 is equal to 0.00284 meters per second.

In this case the velocity is substantially equal to the settling velocity of particles with an aerodynamic equivalent diameter (AED) of 10 micrometers (see graphs 300 and 400). Thus, a majority of particles with an AED larger than 10 micrometers settle out and are not carried on to be measured, but a majority of particles smaller than an AED of 10 micrometers are transported to be measured. This relationship of AED and settling velocity is not an absolute separation. In general, a fifty percent particle cut point will be achieved whereby 50% of the 10 micrometer AED particles in the fluid sample 120 will settle into the basin 155. The balance of particles will be outputted for particulate matter analysis.

As the size of the particle becomes greater than an aerodynamic equivalent diameter of 10 micrometers, an increasing percentage of such particulate matter in the fluid sample 120 will settle into the basin 155 and those particles smaller than a 10 micrometer AED will have a decreasing percentage of settling (an increased percentage will be exhausted from output port 110). This relationship can be represented by the following equation:

$$V = \frac{Q}{A} \quad \text{(equation 1)}$$

where
V=velocity;
Q=flow rate; and
A=cross-sectional area of conduit.

In one embodiment, the cross-sectional area (A) of the conduit 108 is fixed and therefore the flow rate (Q) can be varied to achieve a fluid sample velocity (V) that is equal to the settling velocity of a particle of a given aerodynamic equivalent diameter (AED) and carrier gas temperature.

In accordance with another embodiment, note that the conduit 108 can be configured to include a cross-sectional area that is adjustable. This can be achieved via mechanical manipulation of the conduit 108 (e.g., squeezing or expansion) to adjust the inside diameter of the conduit 108. Thus, assuming the fluid sample 120 is inputted at a substantially constant rate, the diameter of the conduit 108 can be adjusted to change the velocity of the gas in the fluid sample 120 through the conduit 108.

It should be noted that the AED is a commonly used term in aerosol science and technology. This term refers to a diameter that is a measurable index of a particle. When a particle is reported by a technique, the measurement usually corresponds to a specific physical property. For instance, aerodynamic equivalent diameter (a.k.a. aerodynamic diameter) is the diameter of a standard density (1 gram per cubic centimeter) sphere having the same gravitational settling velocity as the particle being measured (which may be of a non-spherical shape and/or non-standard density).

Figure 4:
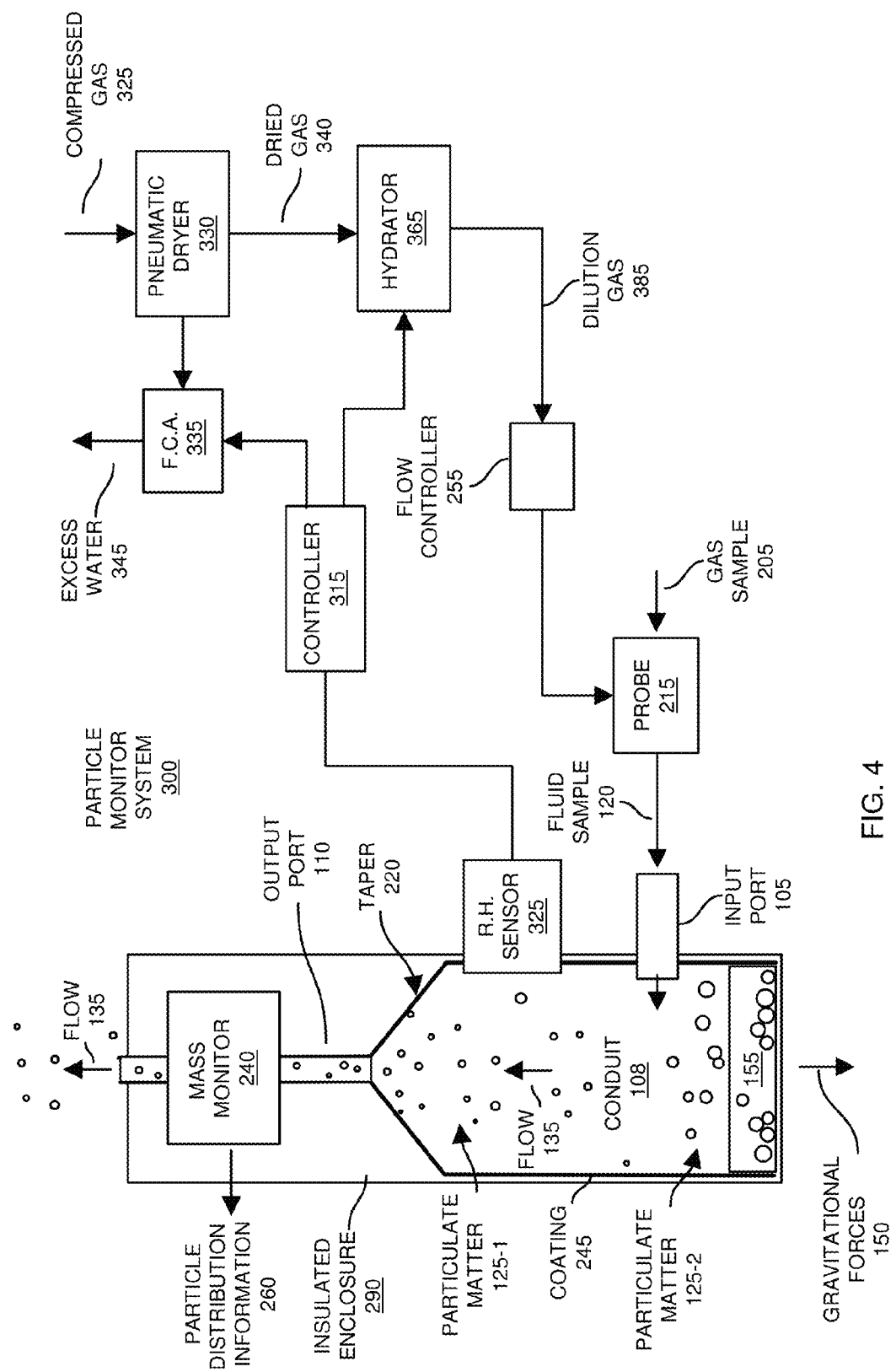

FIG. 4 is an example diagram illustrating relative humidity control according to embodiments herein.

As shown, the particulate monitor system 300 includes many components as previously discussed with respect to earlier figures. Additionally, FIG. 4 includes resources to control a relative humidity of the fluid sample 120 in conduit 108. For example, particulate monitor system 300 includes relative humidity sensor 325, controller 315, flow control assembly 335 (e.g., one or more valves, vents, etc.), pneumatic dryer 330, and hydrator 365.

As its name suggests, relative humidity sensor 325 detects a relative humidity of the fluid sample 120 passing through conduit 108. Controller 315 (e.g., relative humidity controller) monitors the relative humidity of the fluid sample 120 in conduit 108 as indicated by feedback signals received from relative humidity sensor 325.

Based on the feedback signals from relative humidity sensor 325 indicating the relative humidity of the fluid sample 120, the controller 315 controls the relative humidity of dilution gas 385. For example, via the signals received from relative humidity sensor 325, the controller 315 controls the relative humidity of the dilution gas 385. Because the dilution gas 385 is mixed with gas sample 205 to produce fluid sample 120, the adjusting the relative humidity of the dilution gas 385 effectively controls a relative humidity of the fluid sample 120 (which comprises gas sample 205 diluted with dilution gas 385).

During operation, pneumatic dryer 330 receives compressed gas 325. If the relative humidity of the fluid sample 120 as measured by the relative humidity sensor 325 is too high, the controller 315 controls flow control assembly 335 to remove more water from the compressed gas 325 to produce dried gas 340. If the relative humidity of the fluid sample 120 as measured by the relative humidity sensor 325 is too low, the controller 315 controls flow control assembly 335 to remove less or no water from the compressed gas 325 to produce dried gas 340.

The controller 315 can control the hydrator to add water. For example, if the relative humidity of the fluid sample 120 as indicated by relative humidity sensor 325 is too low, the controller 315 adds water to the dried gas 340 via activation of hydrator 365 to produce dilution gas 385. Adding water to the dried gas 340 increases a relative humidity of the dilution gas 385. Conversely, if the relative humidity of the fluid sample 120 is too high, the controller 315 can deactivate the hydrator 365 to prevent addition of water to the dried gas 340. In such an instance, the dilution gas 385 is equivalent to the dried gas 340 without addition of water.

Accordingly, the controller can initiate removal or addition of water to the compressed gas 325 to produce dilution gas 385.

Sample Relative Humidity Control Using Dynamic Dilution Gas Dew Point Control

As previously discussed, a dilution gas 385 can be mixed with the gas sample 205 extracted from a flue to produce fluid sample 120. Via controlling the temperature of the conduit 108, the fluid sample 120 in the conduit 108 equilibrates to the same temperature of the enclosure through the use of thermally conductive wetted components. As mentioned, the conduit 108 can be configured to include a temperature and relative humidity sensing assembly (e.g., relative humidity sensor 325). The temperature of the fluid sample 120 entering the mass monitor 240 can be controlled by controlling the temperature of the output port 110. Also, as mentioned, control of the relative humidity of the fluid sample 120 can be achieved by adjusting the relative humidity of the dilution gas 385.

In accordance with one embodiment, compressed gas such as air is delivered to a pneumatic dryer 330. Any moisture removed from the compressed air can be vented to the atmosphere via flow control assembly 335. By varying the atmospheric venting of moisture from the compressed gas 325, the dew point of the dilution gas 385 is controlled.

As an example, if the moisture of an emission source contains 30% water and the extracted sample is diluted by a factor of 16, the moisture content can be reduced to 1.83% and create a diluted sample of 70% relative humidity at 30 deg C. Should the moisture content of the gas sample 205 decrease, the atmospheric venting can be reduced thereby increasing the dew point of the dilution gas 385 in order to maintain the fluid sample 120 at a substantially constant relative humidity.

In accordance with FIG. 4, in one embodiment, it should be understood that volumetric flow rate within the probe 215 can be held to a substantially constant flow value by holding the dilution ratio constant, thereby supporting the theoretical design for particle penetration for particles of a known size. Variation in the volume of dilution gas 385 through the probe would change the flow regime and may alter the particle penetration efficiency. The feedback loop of relative humidity measurement within the particulate monitor system 300 can facilitate holding or maintaining the relative humidity or dewpoint of the fluid sample to a near or substantially constant reference condition (e.g., 70% relative humidity).

Furthermore, should the relative humidity of the fluid sample 120 fall below the reference condition and the dew point of the dilution gas 385 cannot be raised to a sufficient value via lack of venting via flow control assembly 335, as mentioned, the hydrator 365 can provide the needed moisture back into the dried gas 340. Accordingly, the moisture content of the dilution gas 385 can be controlled to regulate a relative humidity of the fluid sample 120 inputted to conduit 108.

Figure 5:
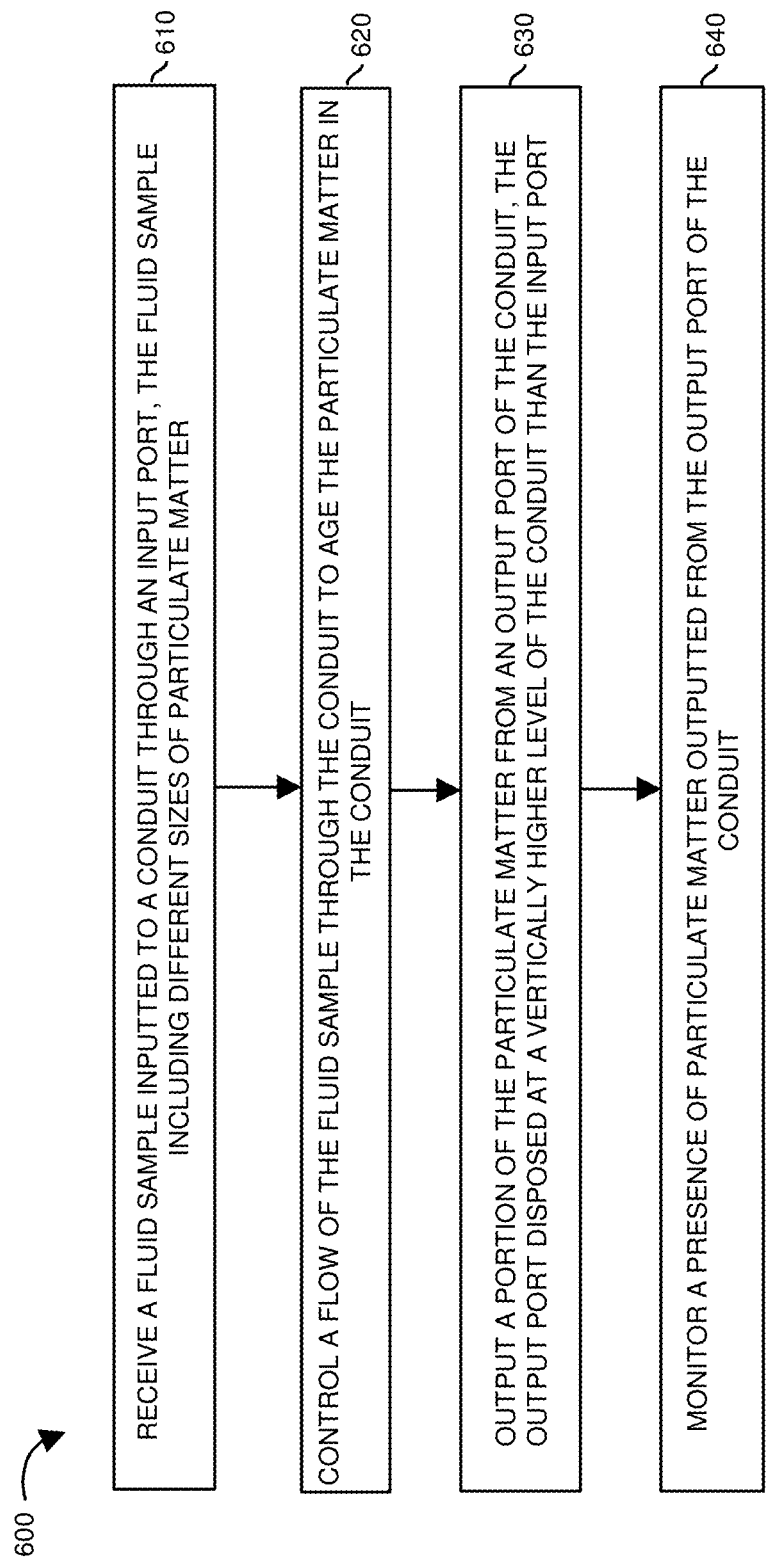
FIG. 5 is a flowchart illustrating an example particulate monitoring method according to embodiments herein.

FIG. 5 is a flowchart 600 illustrating a method of controlling environmental parameters for analyzing a gas sample according to embodiments herein. Note that there will be some overlap with respect to concepts discussed above for FIGS. 1 through 4.

In step 610, the particulate monitor system receives a fluid sample 120 inputted to conduit 108 through an input port 105. The fluid sample 120 includes different sizes of particulate matter.

In step 620, the particulate monitor system controls a flow of the fluid sample 120 through the conduit to age the particulate matter in the conduit 108.

In step 630, the particulate monitor system outputs a portion of the particulate matter from an output port 110 of the conduit 108. The output port 110 is disposed at a vertically higher level of the conduit 108 than the input port 105.

In step 640, the particulate monitor system monitors a presence of particulate matter outputted from the output port 110 of the conduit 108.

Figure 6:
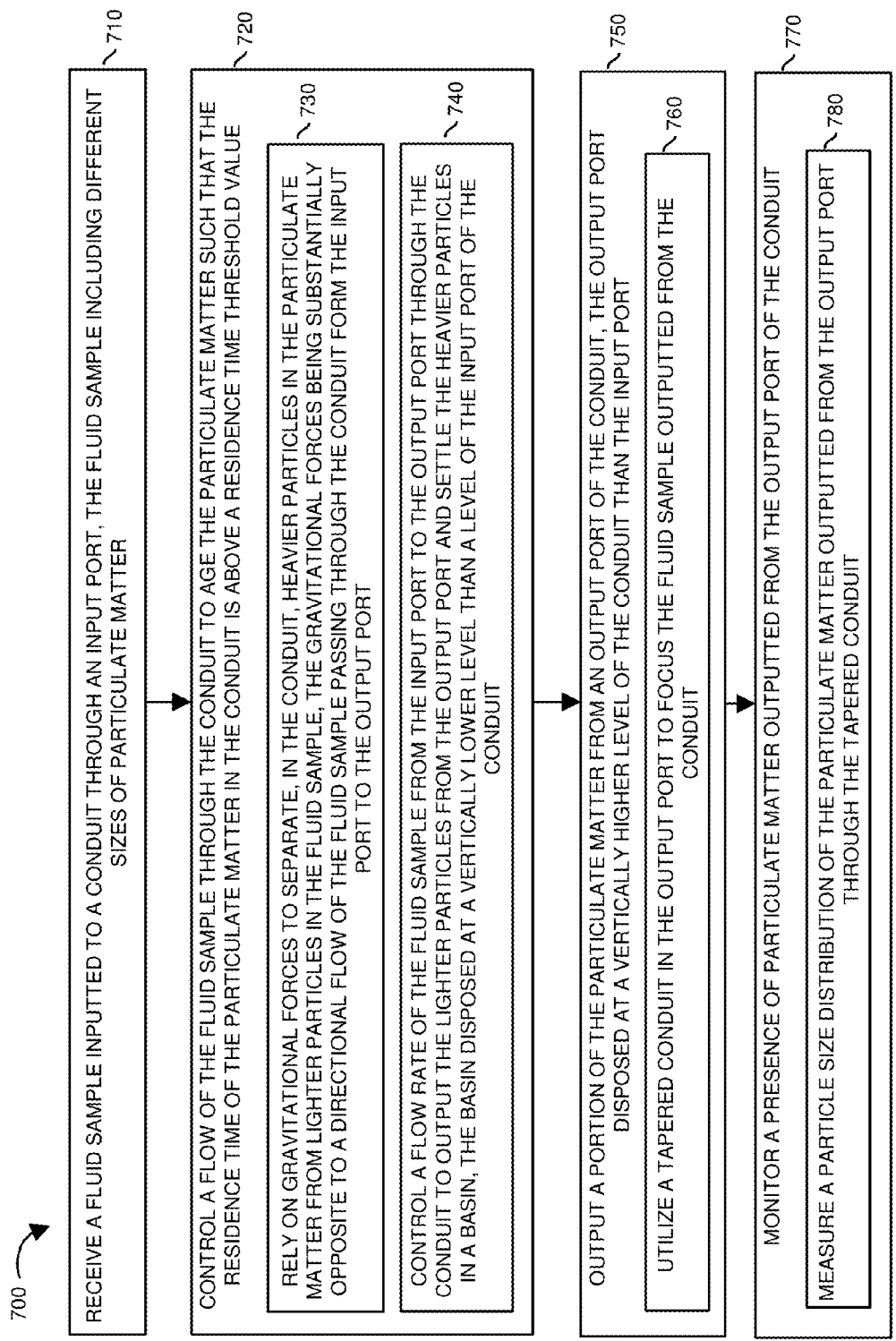
FIG. 6 is a flowchart illustrating an example of particulate matter separation according to embodiments herein.

FIG. 6 is a flowchart 700 illustrating a method of implementing a particulate monitor system according to embodiments herein. Note that there will be some overlap with respect to concepts discussed above.

In step 710, the particulate monitor system receives a fluid sample 120 inputted to a conduit 108 through an input port 105. The fluid sample 120 includes different sizes of particulate matter.

In step 720, the particulate monitor system controls a vertical flow of the fluid sample 120 through the conduit 108 to age the particulate matter such that the residence time of the particulate matter in the conduit 108 is above a residence time threshold value.

In step 730, the particulate monitor system relies on or utilizes gravitational forces to separate, in the conduit 108, heavier particles in the fluid sample 120 from lighter particles in the fluid sample 120. In one embodiment, the gravitational forces are substantially opposite to a directional flow 135 of the fluid sample 120 passing through the conduit 108 from the input port 105 to the output port 110.

In step 740, the particulate monitor system controls a flow rate of the fluid sample 120 from the input port 105 to the output port 110 through the conduit 108 to output the lighter particles (e.g., particulate matter of smaller aerodynamic equivalent diameter having a settling velocity below a threshold value) from the output port 110 and settles the heavier particles (e.g., particulate matter of larger aerodynamic equivalent diameter having a settling velocity above a threshold value) in a basin 155. The basin 155 is disposed at a vertically lower level than a level of the input port 105 of the conduit 108.

In step 750, the particulate monitor system outputs a portion of the particulate matter in the fluid sample 120 from an output port 110 of the conduit 108. The output port 110 is disposed at a vertically higher level of the conduit 110 than the input port 105.

In step 760, the particulate monitor system utilizes a tapered end of the conduit 108 (e.g., taper 220) in the output port 105 to focus the fluid sample 120 outputted from the conduit 120 for analysis by mass monitor 240.

In step 770, the particulate monitor system monitors a presence of particulate matter outputted from the output port 105 of the conduit 108.

In step 780, the particulate monitor system measures a particle size distribution of the particulate matter in fluid sample 120 as outputted through the taper 220 and the output port 105 of conduit 108.

FIG. 7 is a block diagram of an example architecture of a respective computer system 818 such as one or more computers, processes, etc., for implementing any controller functions, analyzer functions, monitoring functions, etc., supported by particulate monitor system according to embodiments herein. In other words, the particulate monitor system can include computer hardware and/or computer software to carry out techniques as discussed herein that are suitable for execution by a computer.

Computer system 818 can include one or more computerized devices such as personal computers, workstations, portable computing devices, consoles, network terminals, networks, processing devices, etc.

Note that the following discussion provides a basic example embodiment indicating how to carry out suitable functionality associated with the particulate monitor system as discussed above and below. However, it should be noted again that the actual configuration for carrying out the particulate matter monitor system can vary depending on a respective application. For example, as previously discussed, computer system 818 can include one or multiple computers that carry out the processing as described herein.

As shown, computer system 818 of the present example includes an interconnect 811 coupling memory system 812, a processor 813, I/O interface 814, and a communications interface 817.

I/O interface 814 provides connectivity to peripheral devices such as repository and other devices 816 (if such devices are present) such as a keyboard, mouse (e.g., selection tool to move a cursor), display screen 830, etc.

Communications interface 817 enables the particulate matter monitor application 840-1 of computer system 818 to communicate over network 890 and, if necessary, retrieve data, update information, etc., from different sources.

As shown, storage 812 can be encoded with instructions associated with particulate matter monitor application 840-1. The instructions support functionality as discussed above and as discussed further below. The particulate matter monitor application 840-1 (and/or other resources as described herein) can be embodied as software code such as data and/or logic instructions on storage 812 such as a tangible and/or intangible computer readable medium, media, etc. such as memory or on another computer readable medium that supports processing functionality according to different embodiments described herein.

During operation of one embodiment, processor 813 accesses storage 812 via the use of interconnect 811 in order to launch, run, execute, interpret or otherwise perform the logic instructions of the particulate matter monitor application 840-1. Execution of the particulate matter monitor application 840-1 produces processing functionality in particulate matter monitor process 840-2. In other words, the particulate matter monitor process 840-2 represents one or more portions of the particulate monitor system performing within or upon the processor 813 in the computer system 818.

It should be noted that, in addition to the particulate matter monitor process 840-2 that carries out one or more method operations as discussed herein, other embodiments herein include the particulate matter monitor application 840-1 itself such as the un-executed or non-performing logic instructions and/or data, etc. The particulate matter monitor application 840-1 may be stored on a computer readable medium (e.g., storage 812) such as a floppy disk, hard disk, an optical medium, etc. According to other embodiments, the particulate matter monitor application 840-1 can also be stored in a memory type system such as in firmware, read only memory (ROM), or, as in this example, as executable code within the storage 812.

Note again that techniques herein are well suited for use in separating and/or aging particulate matter in a fluid sample. However, it should be noted that embodiments herein are not limited to use in such applications and that the techniques discussed herein are suited for other applications as well.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. A method comprising:

receiving a fluid sample inputted to a conduit through an input port, the fluid sample including different sizes of particulate matter, the conduit extending vertically from the input port to an output port, the output port disposed at a vertically higher level of the conduit than the input port;

controlling a vertical flow of the fluid sample through the conduit from the input port to the output port to age the particulate matter resident in the conduit, a portion of the particulate matter resident in the conduit reducing in aerodynamic equivalent diameter size due to the aging;

outputting the portion of the particulate matter in the fluid sample from the output port of the conduit; and monitoring a presence of particulate matter outputted from the output port of the conduit, the method further comprising:

utilizing gravitational forces to separate, in the conduit, heavier particles in the fluid sample from lighter particles in the fluid sample;

wherein the portion is a first portion, the method further comprising:

controlling environmental parameters of the fluid sample in the conduit to simulate aging of the particulate matter in which a second portion of particles in the particulate matter received from the input port physically become heavier particles based on the controlled environmental parameters, the heavier particles settling in a basin of the conduit below the input port due to the gravitational forces as opposed to being otherwise outputted from the output port with lighter particles that are not heavy enough to settle in the basin due to the gravitational forces.

2. The method as in claim 1, wherein the gravitational forces are substantially opposite to the vertical flow of the fluid sample passing through the conduit from the input port to the output port; and wherein outputting the portion of the particulate matter includes outputting the first portion of the particulate matter in a vertical direction through the output port to a mass monitoring system, the vertical direction being substantially similar to a direction of the vertical flow of the fluid sample through the conduit.

3. The method as in claim 1 further comprising:

controlling a flow rate of the fluid sample inputted to the input port of the conduit to: i) separate the heavier particles and the lighter particles from each other in the conduit, ii) output the lighter particles from the output port of the conduit, and iii) settle the heavier particles in the basin, the basin disposed at a vertically lower level than a level of the input port of the conduit.

4. The method as in claim 1 further comprising:

controlling a temperature of the fluid sample in the conduit to age the particulate matter resident in the conduit, the controlled temperature reducing the aerodynamic equivalent diameter associated with the first portion of particulate matter.

5. The method as in claim 1 further comprising:

controlling a relative humidity of the fluid sample in the conduit to age the particulate matter resident in the conduit, the controlled relative humidity reducing the aerodynamic equivalent diameter associated with the first portion of particulate matter.

6. The method as in claim 1, wherein outputting the portion of the particulate matter from the output port of the conduit includes: utilizing a tapered end of the conduit to focus the fluid sample to the output port of the conduit, the tapered end of the conduit increasing a density of the fluid sample as the fluid sample passes from the tapered end of the conduit to the output port; and wherein monitoring the presence of particulate matter outputted from the output port of the conduit includes: measuring a mass concentration of the particulate matter outputted from the output port as received through the tapered end of the conduit.

7. The method as in claim 1, wherein controlling the vertical flow of the fluid sample through the conduit to age the particulate matter includes:

controlling a rate of the fluid sample passing vertically through the conduit such that a residence time of the particulate matter in the conduit is above a threshold value, presence of the particulate matter in the conduit above the threshold value reducing the aerodynamic equivalent diameter size of the first portion of the particulate matter passing through the conduit.

8. The method as in claim 1 further comprising:

receiving the different sizes of particulate matter in the fluid sample through the input port; and controlling a rate of flow of the fluid sample inputted to the conduit through the input port, the rate controlling the vertical flow of the fluid sample through the conduit and which size of the different sizes of particulate matter in the fluid sample in the conduit pass through the output port of the conduit.

9. The method as in claim 1, wherein the fluid sample is a mixture of a gas sample and a dilution gas, the gas sample being a flue gas received from a smokestack, the gas sample including the particulate matter, the dilution gas having a substantially lower concentration of water than a concentration of water in the flue gas.

10. The method as in claim 9 further comprising:

based on monitoring a relative humidity of the fluid sample in the conduit at a location in the conduit between the input port and the output port, adjusting a relative humidity of the dilution gas mixed with the gas sample to maintain the relative humidity of the diluted gas sample in the conduit at a desired level; and monitoring a presence of particulate matter in the diluted gas sample outputted from the conduit.

11. The method as in claim 10, wherein controlling the vertical flow of the fluid sample through the conduit to age the particulate matter includes:

controlling a voluminous rate of inputting the fluid sample into the input port, the voluminous rate controlling a residence time of the particulate matter in the conduit to be above a time threshold value, presence of the particulate matter in the conduit above the time threshold value simulating aging of the particulate matter that would otherwise occur if the fluid sample were exhausted into open atmosphere, the simulated aging reducing the aerodynamic equivalent diameter size of the first portion of the particulate matter passing through the conduit.

12. A particulate monitor system comprising:

a conduit configured to receive a fluid sample through an input port, the fluid sample including different sizes of particulate matter;

a flow controller to control a flow rate of the fluid sample through the conduit to age the particulate matter resident in the conduit, aging of the particulate matter reducing an aerodynamic equivalent diameter of a portion of the particulate matter resident in the conduit;

an output port disposed at a vertically higher level of the conduit than the input port, the output port configured to output a portion of the particulate matter in the fluid sample; and a monitor to analyze a presence of particulate matter outputted from the output port of the conduit;

wherein gravitational forces separate heavier particles from lighter particles in the fluid sample;

wherein the portion is a first portion; and wherein the controller is configured to control environmental parameters of the fluid sample in the conduit to simulate aging of the particulate matter in which a second portion of particles in the particulate matter received from the input port physically become heavier based on the controlled environmental parameters and settle in a basin due to the gravitational forces.

13. The particulate monitor system as in claim 12, wherein the gravitational forces are substantially opposite to a directional flow of the fluid sample passing through the conduit from the input port to the output port.

14. The particulate monitor system as in claim 12, wherein the flow controller controls a flow rate of the fluid sample from the input port to the output port through the conduit to: i) separate the heavier particles and the lighter particles in the conduit, ii) output the lighter particles from the conduit through the output port, and iii) settle the heavier particles in the basin, the basin disposed at a vertically lower level than a level of the input port.

15. The particulate monitor system as in claim 12 further comprising:
a temperature controller to control a temperature of the fluid sample in the conduit.

16. The particulate monitor system as in claim 12 further comprising:
a relative humidity controller to control a relative humidity of the fluid sample passing through the conduit.

17. The particulate monitor system as in claim 12, wherein the conduit includes a tapered end in which to focus the fluid sample for analysis by a mass monitor; and wherein the mass monitor generates information indicating a particle size distribution of particulate matter outputted from the output port.

18. The particulate monitor system as in claim 12, wherein the flow controller controls a rate of the fluid sample through the conduit such that the particulate matter resident in the conduit is present in the conduit above a time threshold value.

19. The particulate monitor system as in claim 12, wherein the flow controller controls a rate of the flow of the fluid sample through the conduit to control which portion of the different sizes of particulate matter in the fluid sample overcome the gravitational forces and pass through the output port of the conduit.

20. The particulate monitor system as in claim 12 further comprising:

a relative humidity sensor disposed in the conduit; and a relative humidity controller configured to monitor a relative humidity of the fluid sample in the conduit, the relative humidity controller controlling a relative humidity of a dilution gas that is mixed with a received gas sample to produce the fluid sample and maintain the relative humidity of the fluid sample in a desired range.

21. The method as in claim 1 further comprising:

controlling environmental parameters of the fluid sample in the conduit to simulate aging of the particulate matter that would occur if the fluid sample was otherwise exhausted into the atmosphere, the controlled environmental parameters including temperature and relative humidity.

22. The method as in claim 21, wherein the aerodynamic equivalent diameter size of the first portion of particulate matter decreases below a threshold value based on the aging.

23. The method as in claim 1 further comprising:

setting the vertical flow rate to a first velocity setting in which a majority of particles, as received in the fluid sample, above a first threshold value pass through output port; and setting the vertical flow rate to a second velocity setting in which a majority of particles, as received in the fluid sample, above a second threshold value pass through output port.

24. The method as in claim 11, wherein the fluid sample is a flue gas received from a smoke stack, aging of the particulate matter in the conduit simulating plume conditions of the flue gas otherwise exiting the smoke stack into the atmosphere.

25. A particulate monitor system comprising:

a conduit configured to receive a fluid sample through an input port, the fluid sample including different sizes of particulate matter, the fluid sample being a flue gas received from a smoke stack;

a flow controller to control a flow rate of the fluid sample through the conduit to age the particulate matter in the fluid sample, aging of the particulate matter reducing an aerodynamic equivalent diameter of a portion of the particulate matter in the fluid sample;

an output port disposed at a vertically higher level of the conduit than the input port, the output port configured to output the portion of the particulate matter in the fluid sample;

a monitor to analyze a presence of particulate matter outputted from the output port of the conduit;

wherein the portion is a first portion;

wherein the flow controller controls a rate of the fluid sample passing through the conduit such that a residence time of the particulate matter in the conduit is above a threshold value, presence of the particulate matter in the conduit above the threshold value increasing an aerodynamic equivalent diameter size of a second portion of the particulate matter in the fluid sample; and wherein the flow controller controls a flow rate of the fluid sample from the input port to the output port through the conduit to change the aerodynamic equivalent diameter of the particles and: i) separate heavier particles in the fluid sample from lighter particles in the fluid sample, ii) output the lighter particles caused by aging from the conduit through the output port, and iii) settle the heavier particles caused by aging in a basin disposed at a vertically lower level than a level of the input port.

* * * * *